(12) United States Patent
Gillette

(10) Patent No.: US 9,788,746 B2
(45) Date of Patent: Oct. 17, 2017

(54) DIAGNOSTIC TESTING HEADBAND

(71) Applicant: Good Sleep, LLC, Grand Blanc, MI (US)

(72) Inventor: Christopher J. Gillette, Battle Creek, MI (US)

(73) Assignee: Good Sleep LLC, Grand Blanc, MI (US)

( * ) Notice: Subject to any disclaimer, the term of this patent is extended or adjusted under 35 U.S.C. 154(b) by 218 days.

(21) Appl. No.: 14/339,073

(22) Filed: Jul. 23, 2014

(65) Prior Publication Data

US 2016/0022211 A1    Jan. 28, 2016

(51) Int. Cl.
*A61B 5/0478* (2006.01)
*A61B 5/00* (2006.01)
*A61B 5/01* (2006.01)
*A61B 5/024* (2006.01)
*A61B 5/0408* (2006.01)

(52) U.S. Cl.
CPC .......... *A61B 5/0478* (2013.01); *A61B 5/4806* (2013.01); *A61B 5/6803* (2013.01); *A61B 5/6814* (2013.01); *A61B 5/6833* (2013.01); *A61B 5/01* (2013.01); *A61B 5/02416* (2013.01); *A61B 5/04085* (2013.01); *A61B 2562/164* (2013.01); *A61B 2562/221* (2013.01); *A61B 2562/226* (2013.01)

(58) Field of Classification Search
CPC ... A61B 5/0478; A61B 5/6814; A61B 5/6831; A61B 5/6803

USPC .......................................... 600/383; 439/909
See application file for complete search history.

(56) References Cited

U.S. PATENT DOCUMENTS

| | | | | |
|---|---|---|---|---|
| 3,735,753 A | * | 5/1973 | Pisarski | A61B 5/0478 600/383 |
| 3,896,790 A | * | 7/1975 | Dikmen | A61B 5/0478 600/383 |
| 4,353,372 A | * | 10/1982 | Ayer | A61B 5/04085 174/117 FF |
| 4,595,013 A | * | 6/1986 | Jones | A61B 5/04085 600/383 |
| 4,638,807 A | | 1/1987 | Ryder | |
| 5,363,858 A | | 11/1994 | Farwell | |
| 5,622,168 A | * | 4/1997 | Keusch | A61B 5/04085 252/500 |
| 6,510,340 B1 | | 1/2003 | Jordan | |
| 8,821,397 B2 | * | 9/2014 | Al-Ali | 600/383 |
| 2007/0208269 A1 | | 9/2007 | Mumford et al. | |
| 2010/0041962 A1 | | 2/2010 | Causevic et al. | |

FOREIGN PATENT DOCUMENTS

EP         2090225 A1 *  8/2009
WO    WO2014/072582 A1 *  5/2014

* cited by examiner

*Primary Examiner* — Lee S Cohen
(74) *Attorney, Agent, or Firm* — Harness, Dickey & Pierce, P.L.C.

(57) ABSTRACT

A diagnostic headband has an elongated body with two ends. A mechanism couples the two ends with one another. At least one first lead is coupled with the body. At least one second lead extends from the body. The leads couple with lead pads on the user. An electrical harness is coupled with the body. The electrical harness electrically couples with the at least one first and second leads.

6 Claims, 4 Drawing Sheets

DIAGNOSTIC TESTING HEADBAND

FIELD

The present disclosure relates to diagnostic testing and, more particularly, to a diagnostic testing headband.

BACKGROUND

When patients do diagnostic testing, such as sleep studies, a wire harness having a plurality of leads is utilized to connect the patient with a testing apparatus. The harness leads are connected with lead tabs positioned upon the patient's body. The wire harness has a connector connected to the testing apparatus measuring different body functions. The wire harness is extremely cumbersome and limits movement of the user. The harness includes very long leads, or wires, and is awkward to manipulate when the patient must move from one position to the other. Accordingly, it is desirable to have a diagnostic testing tool that enables the user to self attach himself or herself to the testing apparatus. Additionally, it is desirable to have an apparatus where the leads are readily accessible to the user. Additionally, it is desirable to have color coded leads to enable the user to readily position the leads onto the proper lead tabs on the user's body.

SUMMARY

Accordingly, the present disclosure provides such a device.

Accordingly to the disclosure, a diagnostic testing headband comprises an elongated body with two ends. A mechanism couples the ends of the body with one another to fit around the user's head. At least one first lead is coupled with the body. The at least one first lead couples with a lead pad contacting the user's head when the body is placed on the user's head. At least one second lead extends from the body to couple with a lead pad on the user. An electrical harness is coupled with the body. The electrical harness electrically couples with the at least one first and second leads. The electrical harness includes a connector to couple with a testing apparatus. A plurality of first and second leads is present. Foam is positioned inside of the body. A first and second leads are color coded. Generally, a hook and loop fastener is utilized to connect the ends of the body together.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 1:
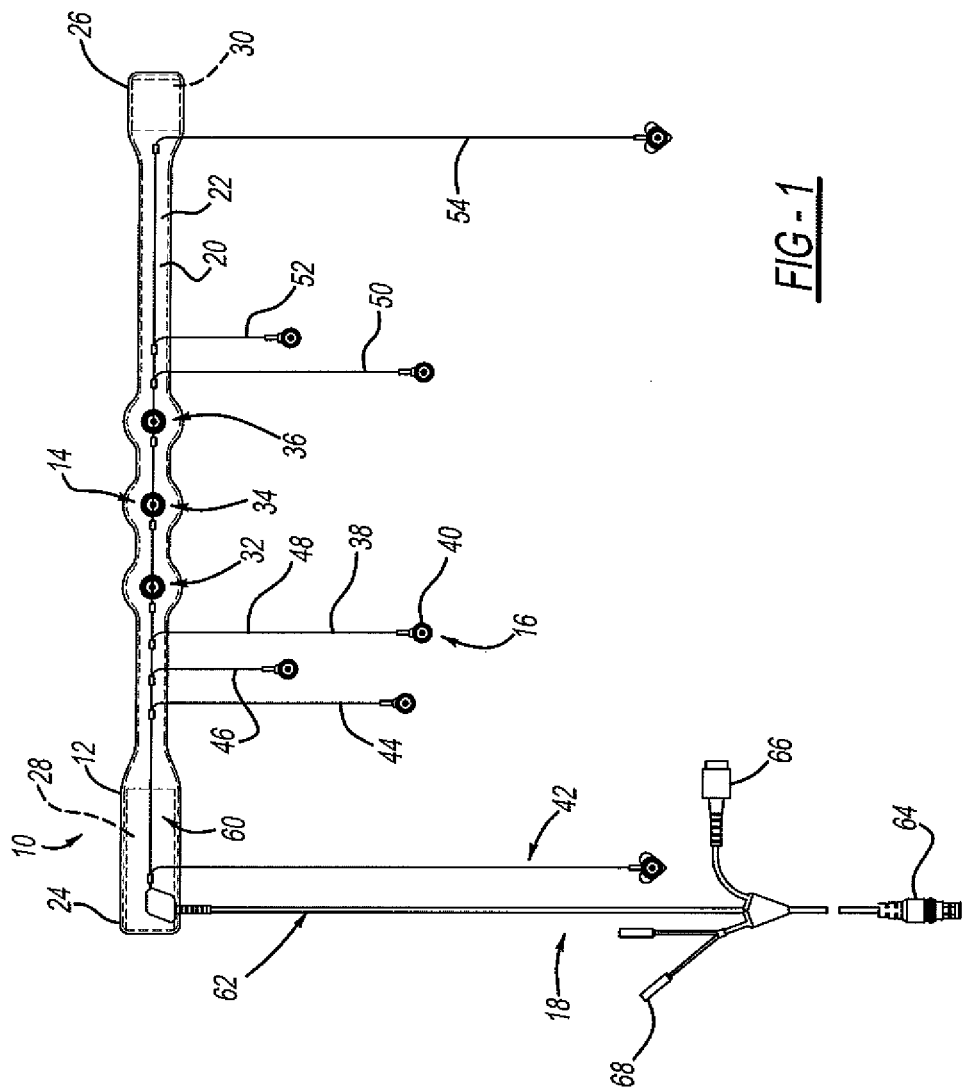
Figure 2:
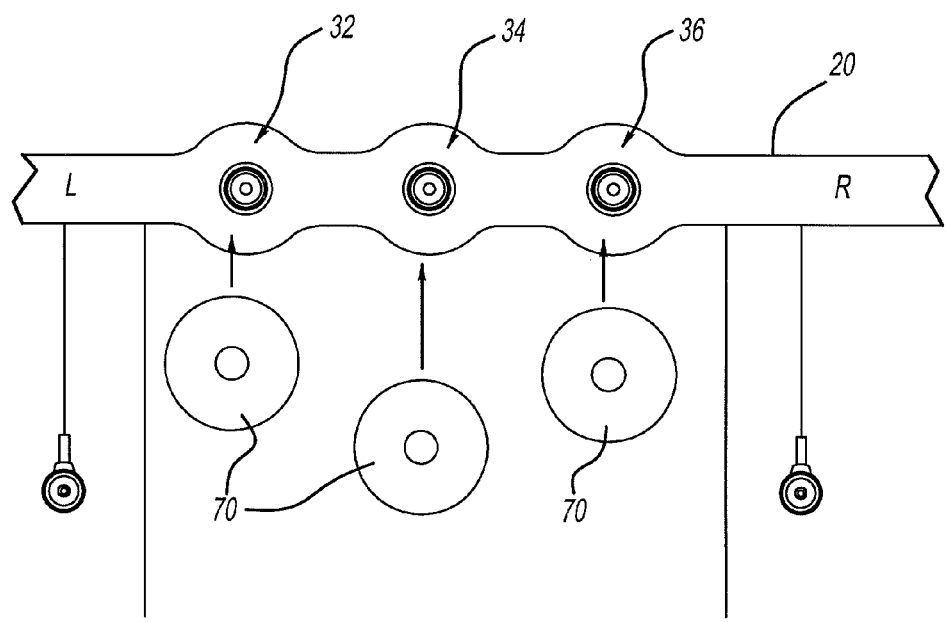
Figure 3:
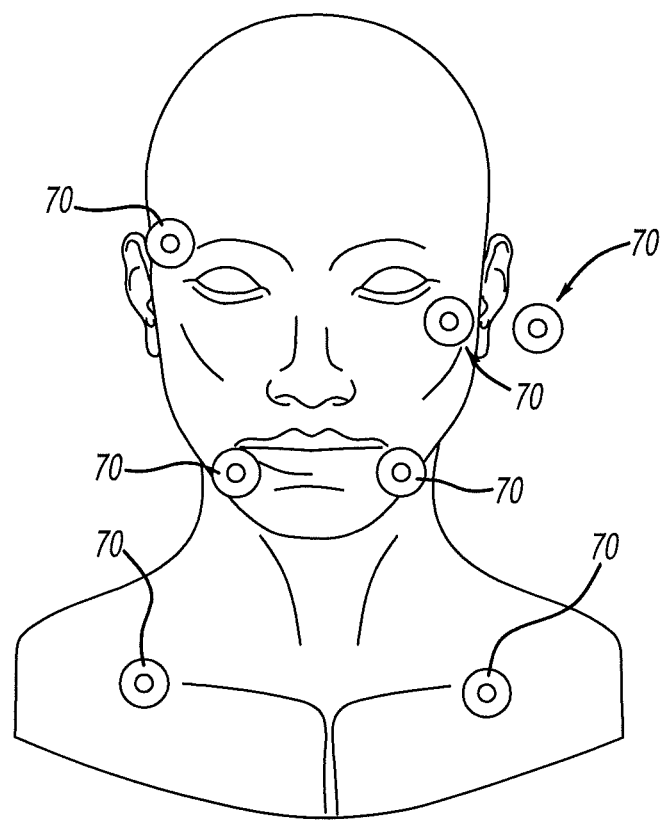
Figure 4:
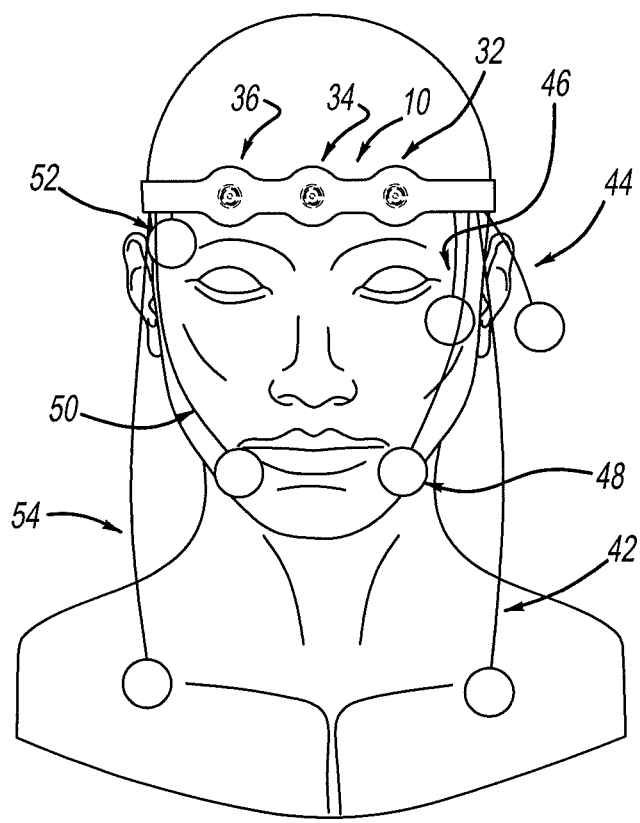

FIG. 1 is a plan view of a diagnostic headband.
FIG. 2 is an enlarged plan view of the headband.
FIG. 3 is a schematic view of the user with the lead pads.
FIG. 4 is a schematic view of the user with the leads attached to the lead pads.

DETAILED DESCRIPTION

Example embodiments will now be described more fully with reference to the accompanying drawings.

Turning to the drawings, a diagnostic headband is illustrated and designated with the reference numeral 10. The headband 10 includes a body 12, a plurality of stationary leads 14, a plurality of extending leads 16 and a wire harness 18.

Turning to FIG. 1, the body 12 is an elongated flexible member. The body 12 generally includes a vinyl or the like covering 20 with a foam insert 22 sandwiched between the covering 20. Thus, the body 12 is flexible and is enabled to wrap around a user's head.

The body 12 includes ends 24, 26. The ends 24, 26 include fasteners 28, 30. Shown are hook and loop fasteners with the hooks at end 28 and the loops at end 30. However, various types of fasteners, such as snaps, hooks and latches, buttons, adjustable straps or the like may be utilized as fasteners to secure the ends of the body 12 together to enable the headband to be wrapped about the user's head.

The body 12 includes at least one stationary lead 14 secured to the body 12. The leads 14, three are shown, are coupled with the body 12. The leads 14 are electrically coupled with the wire harness 18. The leads 14 are color coded with the lead 32 having a center body color coded in yellow. The middle lead 34 is color coded in orange and lead 36 is color coded in red. These leads 32-36 connect with conventional lead tabs that are placed onto the user's forehead.

The at least one extending leads 16 hang from the body 12. The leads 16 include a wire 38 and a lead cap 40. The wires 38 are coupled with the wire harness 18. Thus, in turn, the leads 16 can be coupled with a testing apparatus. The extending leads 16 are illustrated with seven color coded wires 38 and caps 40. Lead 42 has its wire 38 color coded violet with a lead cap 40 having a heart shape. Lead 44 has a blue wire as well as a blue cap 40. Lead 46 is brown with a brown cap. Lead 48 includes a green wire 38 as well as a green cap 40. Leads 42-48 are positioned on one half of the user's body 12. Lead 50 has a white wire 38 as well as cap 40. Lead 52 has a grey wire with a grey cap 40. Finally, lead 54 has a black wire with a black cap. Also, cap 40 of lead 54 has a heart shape. Leads 50-54 are positioned on the other half of the user's body 12.

The harness 18 includes a wire assembly 60 running through the body 12. The wire assembly 60 is coupled with the stationary leads 14 as well as with the extending leads 16. The wire assembly 60 electrically couples the leads 14, 16 with the external wiring assembly tail 62. The tail 62 extends from the body 12. The tail 62 includes a plurality of connectors 64-68. The connector 64 is coupled with a test apparatus. The connector 66 is connected with an oxygen sensor that may be secured onto the user's finger. The connector 68 is connected with a nasal thermistor cannula.

The headband 10 enables the leads to be connected to a user's body, head and, in turn, to the testing apparatus. The headband 10 provides an aesthetic pleasing appearance as well as a non-cumbersome wiring harness. The present tail 62 connector can be removed from the testing apparatus while the leads remain on the user's body (head) so that the user can move easily from one position to a different position.

A method of using the diagnostic headband 10 is as follows. The headband is grasped by the user and positioned so that the stationary leads 14 are directed towards the user. Three lead pads 70 are buttoned into the yellow 32, orange 34, and red 36 leads. The protective backing is kept in place on the pads 70 so that the adhesive surface of the lead pads 70 remains covered. Once buttoned, the three lead pads 70 are in place on the headband 10.

Alcohol prep pad(s) are used to clean the face and behind the ears.

The adhesive lead pads 70 are applied to the user's face and chest. In order to apply the lead pads 70, the protective backing is removed from the lead pad to reveal the adhesive surface. A lead pad 70 is applied to the left side of the user's face, slightly below the left eye.

A lead pad is applied to the right side of the face, slightly above the right eye. A lead pad is applied to the left side of the chin, on the jawbone. A lead pad is applied to the right side of the chin, on the jawbone. The next lead pad is applied behind the left ear. The last two lead pads are attached to the user's chest, on the left and right sides, along the collarbone.

Remove the protective backing from the three lead pads buttoned into the headband. Once the protective backing has been removed, the headband is strapped across the user's head. The middle lead pad contacts the center of the user's forehead. The headband 10 is tightly strapped on the user's head while pressing down the three lead pads in the headband to make sure they are well attached to the user's forehead.

Connect the extending leads 16 to the lead pads 70 applied to the face and chest. The leads are connected in a desired order.

The Purple heart-shaped lead 42 is connected to the lead pad 70 on the left side of the chest. During lead attachment, the lead which the user is instructed to attached should blink back and forth. Blue lead pad alternates with solid color lead pad.

The Black heart-shaped lead 54 is applied to the lead pad on the right side of the chest. The Blue lead 44 is applied to the lead pad behind the left ear. The Brown 46 is applied to the lead pad near the left eye. The Grey lead 52 is applied to the lead pad near the right eye. The Green lead 48 is applied to the lead pad on the left side of the chin. The White lead 50 is applied to the lead pad on the right side of the chin.

A Nasal Thermistor is inserted into the nose so that the single thin wire rests in front of the mouth and route the wires behind the ears. The end of the Nasal Thermistor includes a white lead and a blue lead. Insert the leads into the matching connectors on the main black cable (Blue to blue; white to white).

Leaving all leads and the Nasal Thermistor attached, the Nasal Cannula is inserted into the nose. The hose is routed so that it goes behind the ears.

A pulse-ox finger sensor is attached onto the index finger. The other end of the finger sensor cable is connected to the blue plastic clip attached to the main black cable.

The headband cable and the nasal thermistor hose are connected to the testing apparatus. The end of the nasal cannula hose (transparent plastic tube) is threaded and twists onto the small lead on the bottom of the testing apparatus. The main black cable with the large connector is attached to the testing apparatus by lining up the white dots on the cable tip and the large socket on the bottom of the testing apparatus.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A diagnostic testing headband comprising:
an elongated continuous flexible body with two ends, the body comprising a cover layer and a foam insert sandwiched within the cover layer, a mechanism coupled with the body for connecting the two ends;
at least one first lead stationarily coupled with the body for coupling with conventional lead pads contacting the user's body when the headband is placed on the user's head, the at least one first lead including a mechanism for electrically coupling with the conventional lead pads;
at least one second lead extending from the body for coupling with the conventional lead pads on the user, the at least one second lead including a wire to enable a lead cap to hang from the body and be moved to couple with the conventional lead pads at different positions on the user, the lead cap including a mechanism for electrically coupling with the conventional lead pads; and
an electrical harness coupled with the body such that a portion of the electrical harness is positioned underneath the cover layer and adjacent the foam insert to extend between the first and second leads, the electrical harness electrically coupled with the at least one first lead and with the at least one second lead wire and the electrical harness including a connector for coupling with a testing apparatus.

2. The diagnostic testing headband of claim 1, wherein a plurality of first leads is coupled with the body.

3. The diagnostic testing headband of claim 2, wherein the plurality of first leads is color coded.

4. The diagnostic testing headband of claim 1, wherein a plurality of second leads extend from the body.

5. The diagnostic testing headband of claim 4, wherein the plurality of second leads is color coded.

6. The diagnostic testing headband of claim 1, wherein the mechanism for connecting the two ends of the body is a hook and loop fastener.

* * * * *